(12) United States Patent
Daniol et al.

(10) Patent No.: US 12,354,734 B2
(45) Date of Patent: Jul. 8, 2025

(54) STORAGE SYSTEM AND METHOD FOR STORING MEDICAL PRODUCTS

(71) Applicant: Aesculap AG, Tuttlingen (DE)

(72) Inventors: Mateusz Daniol, Kozlow (PL); Matthias Henke, Villingen-Schwenningen (DE); Lukas Boehler, Furtwangen (DE)

(73) Assignee: Aesculap AG, Tuttlingen (DE)

( * ) Notice: Subject to any disclaimer, the term of this patent is extended or adjusted under 35 U.S.C. 154(b) by 324 days.

(21) Appl. No.: 17/794,096

(22) PCT Filed: Jan. 22, 2021

(86) PCT No.: PCT/EP2021/051514
§ 371 (c)(1),
(2) Date: Jul. 20, 2022

(87) PCT Pub. No.: WO2021/148642
PCT Pub. Date: Jul. 29, 2021

(65) Prior Publication Data
US 2023/0046713 A1 Feb. 16, 2023

(30) Foreign Application Priority Data
Jan. 24, 2020 (DE) .................... 10 2020 101 651.4

(51) Int. Cl.
*G16H 40/20* (2018.01)
*G06Q 10/08* (2024.01)

(52) U.S. Cl.
CPC .............. *G16H 40/20* (2018.01); *G06Q 10/08* (2013.01)

(58) Field of Classification Search
CPC ................................ G16H 40/20; G06Q 10/08
(Continued)

(56) References Cited

U.S. PATENT DOCUMENTS 8,332,240 B1* 12/2012 Garver .................. G16H 20/13
705/2
9,185,501 B2* 11/2015 Pai ........................ H04R 25/554
(Continued)

FOREIGN PATENT DOCUMENTS

KR       101983018 B1    5/2019

OTHER PUBLICATIONS

Search Report received in German Application No. 10 2020 101 651.4 dated Jan. 14, 2021, with translation, 13 pages.
(Continued)

*Primary Examiner* — John H Le
(74) *Attorney, Agent, or Firm* — Christopher A. Rothe; CM Law

(57) ABSTRACT

A storage system for storing medical products, in particular temperature-sensitive medical products, and a method for storing medical products in such a storage system. The storage system includes a storage area with a plurality of storage spaces for a respective type of medical product and at least one sensor for detecting an ambient parameter of the storage area. The storage system has a plurality of sensors, each of which is designed as a data logger and each of which is arranged in a manner specific to the storage space to automatically detect at least one storage space-specific ambient parameter. The storage system has at least one reading device for reading the data loggers.

13 Claims, 1 Drawing Sheet

(58) Field of Classification Search
USPC .......................................................... 702/182
See application file for complete search history.

(56) References Cited

U.S. PATENT DOCUMENTS

| | | | |
|---|---|---|---|
| 9,400,966 B2* | 7/2016 | Dertadian | F25D 3/08 |
| 11,404,151 B2* | 8/2022 | Sandvik | G05B 15/02 |
| 2013/0262337 A1* | 10/2013 | Harel | G06Q 10/08 |
| | | | 705/341 |
| 2019/0073497 A1 | 3/2019 | Burchell et al. | |

OTHER PUBLICATIONS

Search Report received in International Application No. PCT/EP2021/051514 dated Apr. 9, 2021, with translation, 5 pages.
Written Opinion received in International Application No. PCT/EP2021/051514 dated Apr. 9, 2021, with translation, 11 pages.

\* cited by examiner

STORAGE SYSTEM AND METHOD FOR STORING MEDICAL PRODUCTS

CROSS-REFERENCE TO RELATED APPLICATIONS

This application is the United States national stage entry of International Application No. PCT/EP2021/051514, filed Jan. 22, 2021, and claims priority to German Application No. 10 2020 101 651.4, filed Jan. 24, 2020. The contents of International Application No. PCT/EP2021/051514 and German Application No. 10 2020 101 651.4 are incorporated by reference herein in their entireties.

FIELD

The present disclosure relates to a storage system for storing medical products, in particular temperature-sensitive medical products, comprising a storage area with a plurality of storage spaces for a respective type of medical product and at least one sensor for detecting an ambient parameter of the storage area. The disclosure also relates to a method for storing medical products, in particular temperature-sensitive medical products, in such a storage system.

BACKGROUND

In the case of storage/stock-keeping of temperature-sensitive medical products, such as, for instance, drugs and medical supplies, particular storage conditions must usually be observed. Such storage conditions are determined by ambient parameters existing in the store, such as, for instance, temperature, air moisture, and/or light conditions. Both the undercutting and the exceeding of particular limit values/limit parameters of these ambient parameters may result in modifications, impairment and damage of the medical products stored. Depending on the size and type of the store it may be a problem to monitor such ambient conditions for the individual medical products stored there, and to possibly take countermeasures before negative modifications of the products occur. A monitored storage of medical products is especially important against the background of clinical quality monitoring.

From the state of the art, monitoring of the room temperature throughout the storage region is predominantly known. In rare cases, storages are described where a temperature sensor is provided at the good/product to be stored or at individual storage spaces/rack spaces so as to perform a location-specific temperature monitoring (so-called temperature zone monitoring). Here, the exceeding or undercutting of previously defined limit value temperatures may be determined and be evaluated and indicated by a data processing unit.

Moreover, storages are known in which such monitoring is performed and in which the light intensity or the air moisture is detected by interconnected sensors. Such monitoring of light intensity and air moisture is, however, usually performed with respect to the entire store. In the state of the art, the monitoring of individual storage spaces restricts itself usually to the article information and the available number of the respective articles.

KR 101983018 B1, for instance, discloses a logistic store ordering and managing system with a cold chain management function which is adapted to analyze the types of articles to be stored in each store of a store information database. The system is moreover adapted to automatically analyze in which of the plurality of stores and at which position new articles to be stored are stored, in line with the type and volume or types and weight of the new articles to be stored. The system is moreover adapted to inform a manager of the storage company if a temperature detected by a temperature sensor in a store deviates from a proper temperature range of the store concerned, and to effect a change and adjustment of a suitable temperature in line with the storage life of the articles stored in the store.

Storages in accordance with the state of the art have inter alia the following disadvantages. A detection of parameters such as temperature, air moisture, and brightness for the entire store can only produce inaccurate data with respect to individual storage spaces and the conditions prevailing there. This is of disadvantage above all in the case of stores with different products which require different storing conditions, and with large stores. Moreover, usually only momentary/current values of parameters to be monitored are detected and evaluated. Thus, an assessment concerning a future development of these parameters cannot be made. A further disadvantage is that an identification of particular items in store takes place separately from the sensors detecting the storage conditions for these items and hence separately from the data detected with them. Thus, there is a risk that individual requirements applicable for particular products are not considered and observed.

SUMMARY

Against this background it is an object of the present disclosure to reduce the above-mentioned disadvantages of the state of the art and in particular to provide a medical storage system enabling an individual product-specific monitoring and controlling of storage space-specific ambient parameters (zone parameters).

In accordance with the present disclosure this object is solved by a medical storage system, in particular a storage system for storing medical products, preferably of temperature-sensitive and/or light-sensitive and/or moisture-sensitive medical products, comprising:
 a storage area with a number, in particular plurality of storage spaces for a respective type of medical product, and
 at least one sensor for detecting an ambient parameter of the storage area, wherein
 the storage system has a plurality of sensors, each of which is designed as a data logger and each of which is arranged in a manner specific to the storage space, in order to automatically detect at least one storage space-specific ambient parameter, and
 the storage system has at least one reading device for reading the data loggers.

Advantageous embodiments of the disclosure will be explained in detail in the following.

The disclosure advantageously enables an automatic detection of storage space-specific parameter values/ambient parameters (zone parameter values), in particular with respect to temperature and/or light and/or air moisture. It thus also relates to a store monitoring for temperature-critical medical products. Storage space-specific parameters in accordance with the disclosure mean such parameters which exist/prevail at the respective individual storage spaces or products. The subject matter in accordance with the disclosure may advantageously be used especially in smaller high rack storage systems (such as they are, for instance, used in a hospital or a drugstore), where various temperature-critical/temperature-sensitive products/goods are stored jointly.

The disclosure enables in particular a storage space-specific monitoring and possibly controlling/adjusting of ambient parameters of the respective storage space/at the respective storage space and hence a preservation/observation of storage conditions predetermined for long storage life and the avoidance of modification. In a particularly simple way it may especially be taken care that the respective ambient parameter values are always observed and monitored.

The data loggers may especially be adapted to respectively detect at least one of the ambient parameters of temperature, brightness, UV radiation intensity, and air moisture. Preferably, the data loggers are reusable and/or permanently usable in the case of firmly installed data loggers.

The storage system may especially comprise a separate data logger for each storage space. It is particularly preferred if a data logger is arranged at each storage space of the storage system. Arranged in this sense may mean that the respective data logger is installed/applied/mounted firmly at the respective storage space or indirectly or directly at the respective product. The respective data logger may especially be arranged at storage containers such as sterile containers or outside packaging for the products stored. Data loggers disposed at the products stored may, in addition to the current parameter values, also provide an identification of the products stored at a particular storage space. Thus, in addition to its function in the scope of the disclosure, the data logger may also be used for the monitoring of transportation of the products and/or in the scope of cleanings/sterilizations of the medical products.

In accordance with a further embodiment the data logger may be designed respectively for a data communication by means of NFC and/or RFID. Thus, the use of an NFC interface and/or RFID interface for the specific automated reading of detected parameter data or for the specific automated programming of the respective data logger by means of the at least one firmly installed or mobile automated reading device/reader is easily possible.

One embodiment of the disclosure is characterized in that the reading device is firmly assigned to a storage space. Specifically, one respective reading device may be firmly assigned to one respective storage space. Assigned in this sense means in particular that the respective reading device is installed/applied/mounted firmly at the respective storage space. This enables a particularly quick access to the respective data loggers.

Moreover, the storage system may comprise at least one mobile reading device. This reading device may in particular be arranged at a positioning device and may automatically approach the respective storage spaces therewith. The mobile reading device may be arranged at a storage rack in particular by means of an X-Y traversing device. It may comprise a traverse which is adapted to be positioned along the storage rack transversely to its longitudinal direction, and at which the reading device is arranged to be positioned in the longitudinal direction of the traverse. Such an embodiment offers a possibility for the storage space-specific reading of the respective data loggers which is simple and cost-efficient in respects of data and communication.

In other words, in this preferred case a storage system is proposed which is adapted to store medical products, in particular temperature-sensitive and/or light-sensitive and/or moisture-sensitive medical products, comprising a storage space with a plurality of storage spaces for a respective type of medical product, a plurality of sensors, each of which is designed as a data logger and each of which is arranged in a manner specific to the storage space, in order to automatically detect at least one storage space-specific ambient parameter, and at least one reading device for reading the data loggers, wherein the storage system is provided and designed such that the data transmission between a selected data logger and the at least one reading device is performed in the near range (in the sense of a direct/close facing of data logger and reading device) in that either a respective reading device is assigned to each individual data logger and is firmly placed in or at the associated storage space, or at least one individual reading device is approached to the selected data logger by means of a traversing and positioning device and is positioned at a predetermined distance with respect to the selected data logger.

In this manner it may be ensured safely that only data of this one selected data logger are read and the transmission power required for data transmission is relatively low.

Preferably, the storage spaces are each designed such that the storage space-specific ambient parameters are adjustable individually for the respective storage space. Thus, the ambient parameters available at the respective storage space may be changed in particular in real time or almost real time and may especially be controlled by making use of the disclosure. A particular advantage of the disclosure is that such a change/control may take place in manner specific to the storage space, i.e., that a correction of the ambient parameters may be performed at one or a plurality of the storage spaces if required, while other storage spaces with intended ambient parameters remain unchanged. The disclosure thus does not only enable a storage which is specifically tailored to particular products, but also a particularly energy-saving control of the storage system.

The storage system may be designed as a shelf storage system or as a high-bay storage system. The respective storage spaces are then each designed as a shelf compartment.

In accordance with a further embodiment the storage system may also comprise a data processing unit. The storage space-specific data of the ambient parameters which are detected by means of the respective data logger and read by means of the reading device may be transmitted to this data processing unit. The data processing unit is preferably designed for storing, evaluating, and processing these data. A substantial advantage of such a data processing unit is the possibility of storing data concerning the products stored and/or of allocating storage space to the respective product stored. Thus, a simple and efficient identification of the respective products stored and an access to the individual storage conditions applicable for the respective products is possible by a database enquiry, which is a prerequisite for the product-specific adjustment of storage parameters/ambient parameters already mentioned before. The storage of the storage space-specific ambient data detected may be used in an advantageous manner for the evidence of intended storage conditions for the respective products.

In accordance with an embodiment of the disclosure the data of the storage space-specific ambient parameters may be compared with reference parameters stored in the data processing unit. The current storage space-specific ambient parameters may then be corrected or regulated in correspondence with the comparison. Alternatively or additionally, the current storage space-specific ambient parameters may be corrected or regulated by taking a trend development into account. Specifically, trend developments may be calculated by a storage of the parameter values detected. By means of an evaluation of the parameter data stored and by establishing an assessment of a trend development it is possible to efficiently and simply counteract a trend recognized, and to order necessary measures at an early time. A further positive effect is that a possible exceeding or undercutting of predetermined reference parameters/nominal parameters may be detected early and in a storage space-specific/product-specific manner. The initiation of possibly necessary countermeasures may therefore take place quickly and purposefully.

One may say that the storage system consists of data loggers for detecting storage space-specific parameters such as for temperature and/or light and/or air moisture, which data loggers are mounted at the storage spaces or the objects stored. In accordance with one embodiment of the invention the data loggers may each be read via an NFC interface and/or via an RFID interface. Moreover, the data loggers may be read by a reading device/a reader which is either mounted firmly at the respective storage space or which is designed to be mobile and is adapted to approach and read the various data loggers. The data collected by means of the reading device may be transferred to a data processing unit (e.g. in the form of a personal computer) and may be evaluated there. By a storage of the parameter values detected it is possible to calculate trend developments and to detect possible exceeding or undercutting of predetermined reference parameters/nominal parameters at an early time and to take necessary countermeasures. Specifically, if a reading device/reader is installed at each storage space, the storage space-specific data may be read and sent to the data processing unit at defined time intervals. In one embodiment in which a mobile reading device/a mobile reader is used, it may read the logged parameter data at defined time intervals by approaching the storage spaces and may transfer them to the data processing unit. By a simultaneous identification of the object/medical product, with respect to the storage space of which the ambient parameter values were detected, the respective storage conditions may be retrieved by a database and be compared with the current and calculated state.

The disclosure enables especially the following advantages:
- detection of environment conditions directly at the article/medical product for utmost accuracy
- calculation specifically of short-term to medium-term future changes (trends) of the ambient conditions
- use of sensors/data loggers which may also be used outside of the store, for instance, to detect transport conditions
- access to stored nominal conditions/reference parameters for the respective individual articles/medical products
- avoidance of damage due to prediction of negative changes
- reusable data loggers reduce costs
- monitoring may also take place and be evaluated on transport paths
- automatic adaptation of the storage condition to the articles/medical products stored
- autonomous reading enables automated evaluation and adaptation of ambient conditions/ambient parameters Further features and advantages of the present disclosure result from the following exemplary, non-restricting description of the Figures. They are merely of schematic nature and only serve for the understanding of the invention. There show:

BRIEF DESCRIPTION OF THE DRAWING FIGURES

DETAILED DESCRIPTION

Figure 1:
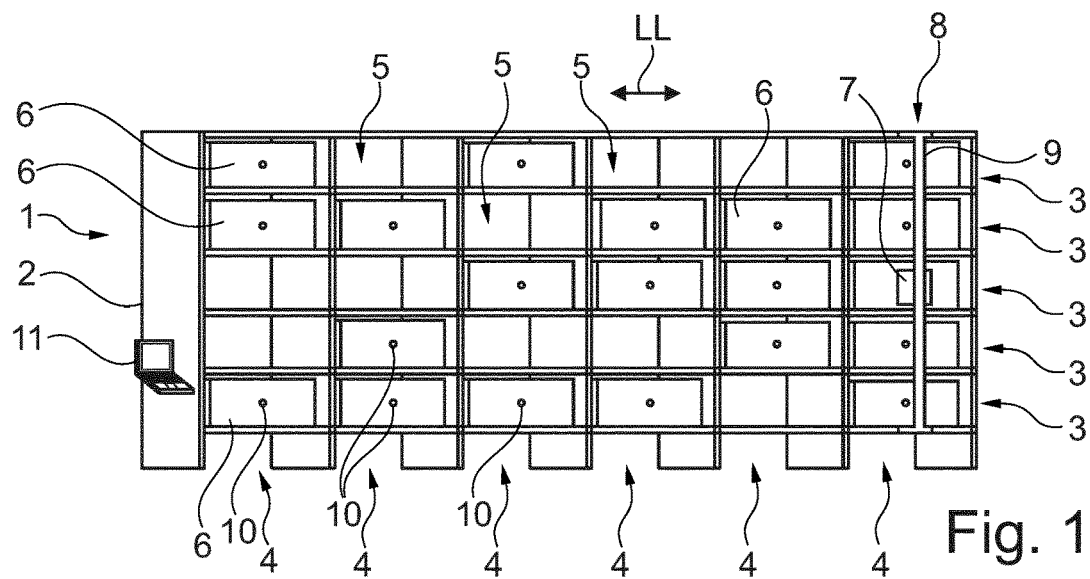
FIG. 1 shows an embodiment of a storage system in accordance with the invention in a schematic perspective view.

FIG. 1 shows an embodiment of a storage system 1 according to the disclosure in a schematic perspective view. The storage system 1 is, for instance, destined as a high-bay storage system for a hospital or a drugstore where various products are stored jointly, and comprises, as a storage area, a shelf 2 with storage spaces/storage zones $5_{x,y}$ arranged in rows 3 and columns 4. In the following description, the parameters x, y used with the reference number 5 serve for the designation of the respective column and/or row of the storage space in the shelf 2. Accordingly, pursuant to the system "storage space $5_{x,y}$ in column x and row y", the storage space $5_{2,3}$ is accordingly positioned in the second vertical column and the third horizontal row (for instance, starting out from the maximally left column and the maximally lower row). The storage spaces/zones $5_{x,y}$ are each destined for the storage of medical products 6. In the illustrated embodiment these are preferably storage containers 6 such as, for instance, sterile containers or transport containers for medical instruments or implants or drugs, etc.

A traversing device 8 (for instance, a robot arm or a combined vertical/horizontal slide) is arranged at the shelf 2, at which at least one (mobile) reading device 7 is arranged. The at least one mobile reading device 7 is adapted to be positioned by means of the traversing device 8 such that the reading device 7 may approach each of the storage spaces $5_{x,y}$ individually. The traversing device 8 comprises, for this purpose, a traverse 9 traversable/positionable at least in the longitudinal direction LL of the shelf 2, which is in turn held to be movable vertically, for instance, at vertical rails indicated at both sides of the traverse 9, and at which the reading device 7 is arranged/mounted to be positionable/traversable like a slide in the longitudinal direction LT of the traverse 9. Furthermore, a drive (not illustrated) for a controlled traversing of the reading device 7 along the traverse 9 and a drive (not illustrated) for a controlled traversing of the reading device 7 in the height direction are provided.

Figure 2:
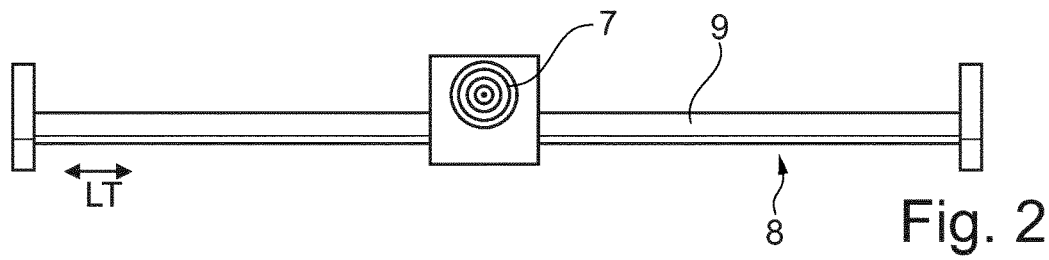
FIG. 2 shows an embodiment of a mobile reading device used in the storage system of FIG. 1.

FIG. 2 shows a detailed view of the traversing device 8 with the reading device 7 arranged thereon. It may be designed in particular as a combined reading-writing-device 7. For autonomous monitoring, the reading device (mobile reader) 7 approaches the corresponding storage spaces $5_{x,y}$ and reads data loggers 10 which are each arranged at the individual storage spaces and/or storage containers 6.

In the embodiment of FIG. 1, each of the products 6, i.e., each storage container 6 or each storage space/storage zone is provided with such a data logger 10. It is adapted and designed for a detection of ambient parameters such as temperature, brightness, UV radiation values, air moisture, etc. As is indicated by way of example in FIG. 1, the reading device 7 is, by means of the traversing device 8, positioned to one of the products 6/transport containers 6 such that it can read and/or program the data logger 10 disposed there. The communication/the data exchange between the data logger 10 and the reading device takes place via NFC and/or RFID.

The storage system 1 further comprises a computing unit (computer) 11 which is, in the Figures, arranged by way of example at the shelf 2, but will in reality usually be arranged separately therefrom. The computing unit 11 is in data communication with the reading device 7 and the traversing device 8 and serves in particular for the storage of ambient parameters detected by means of the data loggers 10 and of corresponding reference parameter values, the monitoring of the storage space-specific ambient parameters and possibly their correction/regulation/control by means of the reference values stored, and possibly the general store administration with equipment, input and/or output check.

Figure 3:
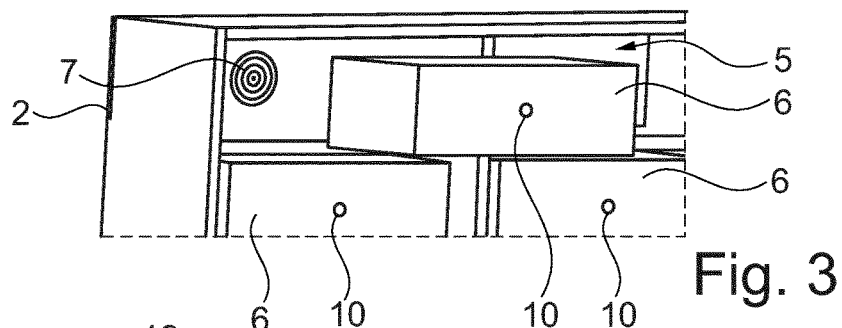
FIG. 3 shows a section of the storage system of FIG. 1 with a firmly installed reading device.

FIG. 3 shows a further embodiment of the disclosure in a section. Deviating from the embodiment of FIG. 1, here a respective stationary, firmly installed reading device 7 is arranged at each of the storage spaces $5_{x,y}$. Each of the reading devices 7 is designed to read/program the data logger 10 of the respective storage container 6 which is currently positioned in the corresponding storage space/storage zone.

Figure 4:
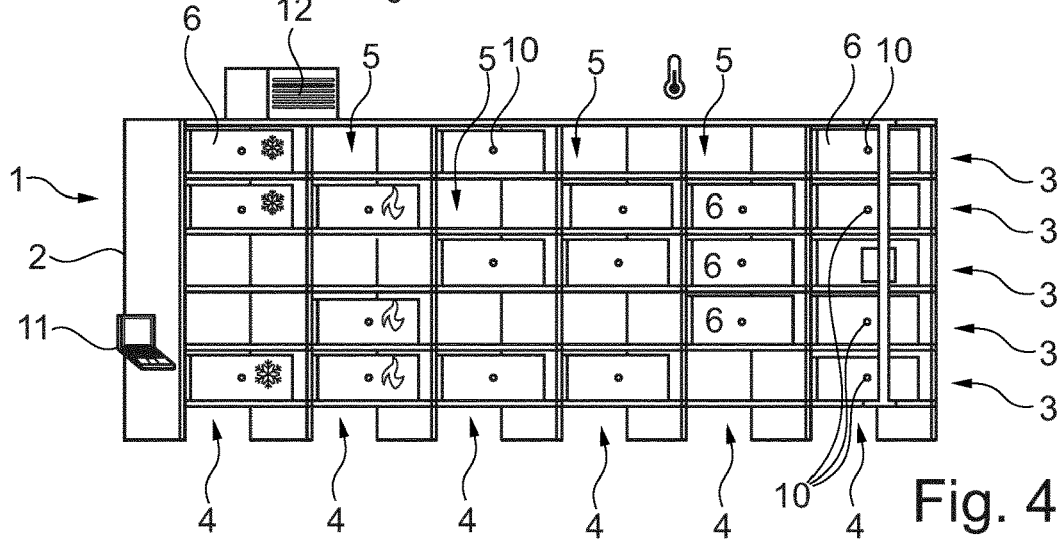
FIG. 4 shows a further embodiment of a storage system in accordance with the invention in a schematic perspective view.

FIG. 4 illustrates that, by means of the disclosure, the respective ambient parameters available at each of the storage spaces $5_{x,y}$, such as here, for example, the temperature, may be adjusted/regulated/controlled. The average storage temperature is, for instance 25° C. By means of an air conditioning unit 12 each of the storage spaces $5_{x,y}$ may be air-conditioned individually and independently of the other storage spaces 5. So, the storage spaces $5_{1,x}$ of the first column from the left in FIG. 4 are cooled since the products there are heat-sensitive, namely the upper storage space $5_{1,1}$ to a temperature of 5° C., the storage space $5_{1,2}$ positioned therebelow to a temperature of 10° C., and the lower storage space $5_{1,5}$ to a temperature of 15° C. The storage spaces $5_{2,y}$, however, are heated since the medical products 6 there are sensitive to coldness. The storage space $5_{2,2}$ is heated to 30° C., the storage space $5_{2,4}$ is heated to 35° C., and the storage space $5_{2,5}$ is heated to 35° C.

The invention claimed is:

1. A storage system designed for storing medical products, the storage system comprising:
   a storage area comprising storage spaces for a respective type of said medical products;
   a plurality of sensors, each of which is designed as a data logger and each of which is arranged in a manner specific to a respective storage space, in order to automatically detect at least one storage space-specific ambient parameter; and
   at least one reading device for reading the data loggers, wherein the storage system is provided and designed such that a data transmission between a selected data logger of the data loggers and the at least one reading device takes place by the at least one reading device directly facing the selected data logger, wherein the at least one reading device is approached to the selected data logger by an automated traversing and positioning device and is positioned at a predetermined distance with respect to the selected data logger, and wherein the data loggers are each designed for a data communication by NFC, and wherein the at least one reading device is adapted to be positioned by means of the automated traversing and positioning device such that the at least one reading device may approach each of the storage spaces individually.

2. The storage system according to claim 1, wherein the at least one storage space-specific ambient parameter comprises temperature, brightness, UV radiation intensity, or air moisture.

3. The storage system according to claim 1, wherein each storage space comprises one of the data loggers such that one of the data loggers is arranged at each storage space.

4. The storage system according to claim 3, wherein one of the data loggers is firmly installed at each storage space, and/or one of the data loggers is arranged at a medical product stored in each storage space.

5. The storage system according to claim 1, wherein the storage spaces are each designed such that the at least one storage space-specific ambient parameter is individually adjustable.

6. The storage system according to claim 1, wherein the storage system is a shelf storage system or a high-bay storage system and the storage spaces are each designed as a shelf compartment.

7. The storage system according to claim 1, further comprising a data processing unit to which storage space-specific data of the at least one storage space-specific ambient parameter detected by one of the data loggers and read by the at least one reading device is transmitted, and which is designed for evaluation and processing of said storage space-specific data.

8. The storage system according to claim 7, wherein the data processing unit is configured to:
   detect storage space-specific ambient parameters at defined time intervals; or
   read storage space-specific data from the data loggers at defined time intervals.

9. The storage system according to claim 8, wherein the data processing unit is configured to:
   compare data of the at least one storage space-specific ambient parameter and a reference parameter stored in the data processing unit; and
   correct or regulate the at least one storage space-specific ambient parameter based on a comparison of the at least one storage space-specific ambient parameter and the reference parameter or a trend development.

10. The storage system according to claim 8, wherein the storage system is designed to store temperature sensitive medical products.

11. The storage system according to claim 1, wherein the storage system is designed to store temperature sensitive and/or light sensitive and/or moisture sensitive medical products.

12. The storage system according to claim 1, wherein the predetermined distance is selected to allow data communication between the at least one reading device and the selected data logger at a specific one of the storage spaces.

13. The storage system according to claim 1, wherein the at least one reading device is provided and designed to communicate by NFC with only the selected data logger when the at least one reading device is directly facing the data logger.

* * * * *